United States Patent [19]
Prota et al.

[11] Patent Number: 5,441,542
[45] Date of Patent: Aug. 15, 1995

[54] PROCESS AND KIT FOR POST-OXIDATIVE TREATMENT OF PERMANENTLY DYED HAIR

[75] Inventors: Giuseppe Prota, Naples, Italy; Gottfried Wenke, Woodbridge, Conn.

[73] Assignee: Clairol Incorporated, Stamford, Conn.

[21] Appl. No.: 174,487

[22] Filed: Dec. 27, 1993

Related U.S. Application Data

[63] Continuation-in-part of Ser. No. 159,988, Nov. 30, 1993, and a continuation-in-part of Ser. No. 766,606, Sep. 26, 1991, Pat. No. 5,273,550, and a continuation-in-part of Ser. No. 909,371, Jul. 13, 1992, Pat. No. 5,279,617, and a continuation-in-part of Ser. No. 923,078, Jul. 31, 1992, Pat. No. 5,279,618.

[51] Int. Cl.$^6$ .............................................. A61K 7/13
[52] U.S. Cl. ...................................... 8/406; 8/424; 8/624
[58] Field of Search .................... 8/405, 406, 424, 624

[56] References Cited

U.S. PATENT DOCUMENTS

| | | | |
|---|---|---|---|
| 2,875,769 | 3/1959 | Rosmarin et al. | 132/7 |
| 2,944,869 | 7/1960 | Kalopissis et al. | 8/11 |
| 3,698,852 | 10/1972 | Pantzer et al. | 8/10.2 |
| 3,993,436 | 11/1976 | Fujinuma | 8/10.2 |
| 4,453,941 | 6/1984 | Jacobs | 8/405 |
| 4,746,322 | 5/1988 | Herlihy | 8/405 |
| 4,904,274 | 2/1990 | Schultz et al. | 8/406 |

Primary Examiner—Paul Lieberman
Assistant Examiner—Caroline L. Dusheck
Attorney, Agent, or Firm—Charles J. Zeller

[57] ABSTRACT

A process for increasing the amount of melanin formation following hair dyeing by ferricyanide oxidation of a dopa species hair colorant utilizing a post-oxidant such as sodium periodate at a controlled pH and compositions and kits for use in the process.

12 Claims, No Drawings

PROCESS AND KIT FOR POST-OXIDATIVE TREATMENT OF PERMANENTLY DYED HAIR

RELATED APPLICATIONS

This application is a continuation-in-part of copending and commonly owned patent applications Ser. No. 08/159,988; Ser. No. 07/766,606, U.S. Pat. No. 5,273,550; Ser. No. 07/909,371, U.S. Pat. No. 5,279,617; and Ser. No. 07/923,078, U.S. Pat. No. 5,279,618 filed Nov. 30, 1993; Sep. 26, 1991; Jul. 13, 1992 and Jul. 31, 1992 respectively. The complete disclosures of these applications are incorporated herein by reference.

FIELD OF THE INVENTION

The present invention relates to improvements in the use of dopa (3,4-dihydroxyphenylalanine) and or substituted dopa (together "dopa species") to generate melanin pigments to dye hair permanently. More specifically, the present invention relates to an oxidative treatment of hair which has been permanently dyed with melanin by oxidation of at least one melanin precursor with a ferricyanide oxidant. Said oxidative treatment is hereinafter referred to as a post-oxidative treatment.

The above described related applications describe hair dyeing processes wherein the dopa species and a ferricyanide oxidant react in an aqueous environment to provide unexpectedly high concentrations of one or more nitrogenous phenolic, especially indolic, melanin precursors in the aqueous environment, the melanin precursors formed during the reaction being effective to dye hair permanently upon their coincident conversion to melanin (as hereinafter defined) while in the hair. The dopa species may be employed together with one or more hair dye modifiers selected from direct dyes, primary intermediates, couplers and mixtures thereof. In addition, the applications describe methods of dyeing hair wherein the melanin is generated by the user from separately packaged reactants sold in the form of a kit.

It has now been discovered that it is possible to increase the amount of melanin formation thereby increasing the intensity of the hair coloring by a post-oxidative treatment of the hair with additional oxidizing agent. The post-oxidation procedure is conducted after rinsing the hair. Its effect is to oxidize melanin precursors which have migrated into the hair strand but have not been completely converted to melanin by the initial treatment. Any of a number of post-oxidants can be employed, the preferred being an alkali metal periodate. It is especially preferred to use a mixture of post-oxidant and a surfactant so that increased melanin formation and shampooing can be conducted simultaneously.

BACKGROUND OF THE INVENTION

As reported, for example, in Prota, *Progress in the Chemistry of Melanins and Related Metabolites*, Med. Res. Reviews, 8:525–56 (1988), melanins are naturally occurring pigments present in hair and skin. In humans, biosynthesis takes place in tyrosinase containing melanocytes. The tyrosinase enzyme catalyzes the hydroxylation of tyrosine to dopa and its subsequent oxidation to dopachrome. Once formed, dopachrome undergoes a series of complex reactions in the formation of eumelanins and phaeomelanins.

Melanins provide black and deep brown pigments, and are formed by oxidative polymerization of 5,6-dihydroxyindole derived biogenetically during the melanogenesis. On the other hand, phaeomelanins provide yellow to reddish brown pigmentation to hair and are formed by oxidative polymerization of cystein-S-yl-dopas via 1,4-benzothiazine intermediates.

Synthetic 5,6-dihydroxyindole (DHI) has been disclosed in the prior art for use in hair and skin dyeing. For example, U.S. Pat. No. 2,934,396 to Charle discloses a process for dyeing hair by contacting hair with an aqueous solution of DHI having a pH of at most 7 for 5 to 60 minutes, followed by an application of an aqueous solution capable of inducing oxidation and/or polymerization of DHI.

Dopa and dopamine are disclosed as hair dyeing precursors in the process of Herlihy, U.S. Pat. No. 4,746,322, wherein the aqueous hair dyeing composition comprises said precursor, an organic compound to assist dye dispersion and an iodate or periodate oxidant.

Interest in melanogenesis to dye hair is quite high. This is because synthetic melanin pigments provide an exceptionally natural-looking deep brown or black color. Moreover, they are not irritating to the skin, nor are they mutagenic.

The discovery of the formation of melanin pigments for permanent hair coloration by oxidation with ferricyanides has proved to be very useful. It has now been found, quite suprisingly, that the results achieved with the ferricyanide oxidation can be appreciably improved by a post-oxidation treatment to increase melanin formation.

The hair dyeing process of the present invention contemplates as an initial step the preparation of an aqueous hair dyeing composition by reacting a dopa species as hereinafter defined, with a ferricyanide oxidant to form a melanin-forming hair dye precursor, and applying the aqueous composition to the hair. The melanin precursor contained in said aqueous composition is capable of diffusing into the hair shaft in an amount effective to dye hair permanently upon its coincident conversion to melanin while in the hair.

The aqueous hair dyeing composition is produced by initiating reaction between the dopa species or a salt thereof with an inorganic oxidant that is a soluble ammonium, alkali or alkaline earth metal salt, especially a sodium or potassium salt, of ferricyanide in an aqueous reaction medium buffered by sufficient buffering agent to maintain the reaction medium pH from about 6 to about 11 throughout the series of reactions that take place leading to the melanin precursor.

In order to achieve the permanent dyeing of hair with a ferricyanide oxidant, it is critical to generate melanin from the melanin-forming hair dye precursor in the aqueous hair dye composition in such amount as to effect a color change to the hair. It is further critical that the hair dye composition be applied to the hair prior to the substantial formation of melanin so that the melanin precursor formed during the reaction may diffuse into the hair prior to the generation of melanin, the melanin then being formed within the hair.

In the case in which the dopa species is dopa or a salt thereof, the reaction with the oxidant leads to the formation of 5,6-dihydroxyindole, which melanin precursor, upon its conversion to melanin, provides hair with a permanent black color. In the case of other dopa species, melanin precursors are obtained which, upon conversion to melanin, produce a range of shades depending upon the selection of the substituted dopa compound.

A further aspect of the ferricyanide oxidation process is the optional incorporation of an oxidative hair dye component selected from the group consisting of direct dyes, primary intermediates, couplers and mixtures thereof in the reaction mixture. Following the initial dopa species-oxidant reaction, it is believed that the direct dyes, primary intermediate(s) and/or coupler(s) present in the reaction mixture react at least in part with the intermediate compounds formed prior to the melanin precursor, thereby providing chromatic characteristics to the melanins ultimately obtained.

In another aspect of the ferricyanide oxidation method, the rate of formation of indolic melanin precursors such as 5,6-dihydroxyindole is hastened by proper selection and amount of the buffer, apart from its requirement for maintaining pH of the reaction medium. Preferably, the buffer is a phosphate, carbonate or bicarbonate, and typically is included in substantial excess over the amount needed to maintain the requisite pH.

It has also been observed that the rate of melanin formation improves by treatment of the hair with agent(s) that promote melanin formation, e.g., a solution of a metal ion salt.

It has now been found that the ferricyanide process in all of its variations can be improved by a post-oxidative treatment of the melanin dyed hair utilizing, preferably sodium periodate.

The improved process of the present invention may conveniently be practiced by providing premeasured amounts of the reactants in separate containers packaged in kit form. The user simply admixes the reactants and utilizes the mixtures in accordance with the procedures described herein. No special expertise is required to carry out the process, and accordingly the product and process are equally suitable for in-home use by the nonprofessional as well as salon use by the professional. Advantageously, the product in kit form is shelf-stable and is therefore suitable for retail sale and without precautions generally required for melanin-forming precursors, such as 5,6-dihydroxyindole, e.g., storage under anaerobic conditions.

DETAILED DESCRIPTION OF THE INVENTION

Since this invention is an improvement in the ferricyamide process, and the latter is an essential first step in the invention, there follows a detailed description of that process to be followed by a detailed description of the post-oxidation process.

The ferricyanide hair dyeing process comprises the preparation of an aqueous hair dyeing composition by reacting a dopa species or mixture thereof, and an inorganic oxidant, optionally in the presence of an oxidative hair dye modifier selected from the group consisting of direct dyes, primary intermediates, couplers, and mixtures thereof and contacting the hair with said hair dyeing composition for a period of time, typically less than one hour, said reaction proceeding in such manner and under such conditions as to provide in the hair an amount of a melanin-forming hair dye precursor during the period of contact effective to generate a hair dyeing amount of melanin. The precursor diffuses into the hair during the period of contact and forms melanin in situ in the hair to provide a permanent color. Preferably, the contact time of the hair dyeing composition on the hair is from about 5 to about 45 minutes, most preferably from about 5 to about 30 minutes.

By "permanent" is meant a color not removable by shampooing with a conventional surfactant-containing shampoo, the permanency being attributable to the inability of melanin and the melanin precursors to diffuse from the hair shaft in view of their molecular size.

By "melanin" is meant a synthetically derived pigment formed by polymerization of a melanin precursor, i.e., the formation of molecules too large to be removed from the hair.

By "melanin-forming precursor" is meant the reaction product(s) of the dopa species with a ferricyanide oxidant and optionally with a direct dye, primary intermediate or coupler hair dye component, which reaction product(s) undergoes polymerization to form melanin. Such melanin precursors generically are nitrogenous phenolic compounds and are indolic compounds, except to the extent that cyclization to form the indole ring might be prevented in view of reactions occurring with direct dyes, couplers and/or primary intermediates, as hereinafter disclosed.

Applicants herein believe that the terms "melanin" and "melanin precursor" as used herein with respect to the reaction products of the selected dopa species of this invention art terms which are well understood by one of ordinary skill in the field, even though the chemical identity of the melanin precursors, particularly those precursors formed by reaction with direct dyes, primary intermediates and/or couplers, and especially the melanins formed in accordance with the process of the present invention, may not be precisely known or understood.

As will be described more fully hereinafter, the reactants employed in this invention may be provided in kit form, for admixture by the user. It is possible to combine the reactants directly on the hair of the user, but preferable to mix them in a mixing vessel, for subsequent application to hair following commencement of the reaction.

It has been found that the color obtained by ferricyamide oxidation of the dopa species can be significantly modified by including direct dyes, primary intermediates and/or couplers in the reaction medium. In this regard, the terms "melanin precursor+ and "melanin" are intended to include reaction products of primary intermediates and couplers with the dopa species and with reaction products of the dopa species produced by oxidation with the oxidant. While such melanin precursors are nitrogenous phenolic compounds, it is not known whether they have an indole ring in their chemical structure.

The hair dyeing process with ferricyanide involves a series of reactions leading to the formation of one or more melanin precursors capable of diffusing into the hair shaft. Within the hair shaft, the precursor may be oxidized by air to melanin, which is incapable of diffusion into or from the hair shaft. Accordingly, the melanin precursor-containing hair dye composition must be applied to the hair prior to the substantial formation of melanin. Inasmuch as the precursor, upon formation, will begin its conversion to melanin by reaction with air, it is critical to apply the reaction medium to hair prior to onset of substantial melanin formation, that is, at or shortly after admixture of the reactants. In the process of this invention, the oxidation of substantially all of any melanin precursor to melanin is completed by the post-oxidative treatment.

The term "applying" as used herein means the contact between the selected hair dye composition and the hair as described above. Placing the hair dye composition on the hair following substantial melanin formation is not operable since the insoluble melanin will not diffuse into the hair, and will be largely stripped away during subsequent shampooing. For convenience, a contact time of "less than about one hour" as used throughout this application is measured from the onset of mixing of the reactants.

It should also be understood that suitable aqueous hair dyeing compositions whether for ferricyanide oxidation or post-oxidative treatment can be obtained without adding additional constituents to the aqueous reaction medium. As described below, however, it is preferred to include additional optional constituents, e.g., thickeners, etc., to provide a more elegant product.

In the initial step of the present invention, the dopa species is oxidized by the oxidant through a series of reactions leading to the formation of one or more melanin precursors. While not wishing to be bound by any particular reaction scheme, applicants herein believe that the following reactions occur leading to the formation of the melanin precursors: (1) oxidation of the dopa species by the ferricyanide oxidant followed by cyclization, further oxidation and rearrangement with carbon dioxide release, leading to the formation of an indole, e.g., the conversion of dopa to 5,6-dihydroxyindole, (2) oxidation of the dopa species followed by cyclization, further oxidation and rearrangement without carbon dioxide release, and (3) reactions wherein the initial dopa species oxidation product(s) is modified by further reaction with a coupler or primary intermediate, leading to nonindolic nitrogeneous phenolic compounds.

In the case of dopa, for example, dopa is oxidized to dopaquinone, which spontaneously forms cyclodopa. Additional oxidant further reacts with the cyclodopa to form dopachrome which undergoes spontaneous, although not immediate, transformation to 5,6-dihydroxyindole through rearrangement of the dopachrome species and the release of carbon dioxide. Analogous reactions also take place with regard to alpha alkyl dopas. Dopa alkyl esters also react similarly, but without release of carbon dioxide. The reactions for the preparation of melanin from dopa as these reactions are presently understood are presented below.

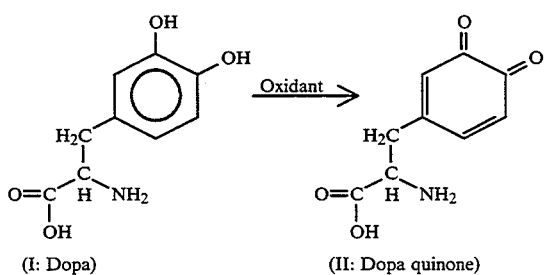

(I: Dopa)  (II: Dopa quinone)

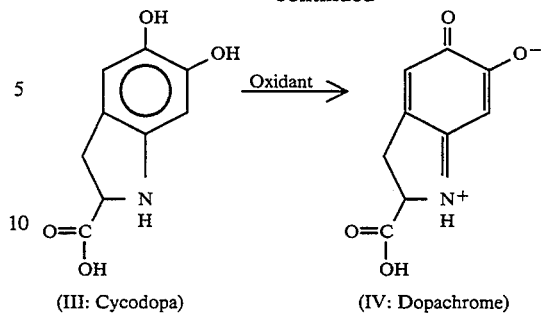

(III: Cycodopa)  (IV: Dopachrome)

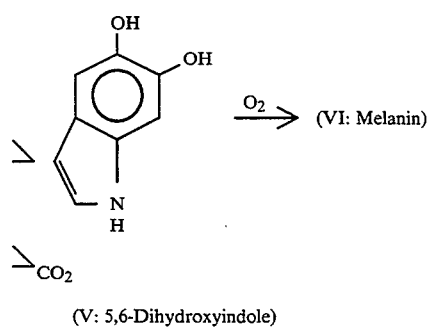

(V: 5,6-Dihydroxyindole)

The Dopa Species

As previously indicated, the preparation of the aqueous hair dye composition is by the consumer, who admixes the reactants at the time of use. The dopa species or a suitable salt thereof is present in the initial reaction medium at a level suitable to obtain a hair dyeing amount of melanin, which melanin amount, in turn, is dependent on the melanin intermediate levels achieved during the period of contact of the hair dyeing composition with the hair.

The required initial dopa species concentration in the reaction medium may be higher than its solubility limit in water. Accordingly, an acid or alkaline aqueous premix can be prepared prior to preparation of the aqueous reaction medium. Alternatively, the more soluble acid or basic salts can be used in the preparation of the aqueous medium. Use of the salts or the use of an acid or alkaline premix allows the otherwise relatively insoluble dopa reactant to go into solution and be available for rapid reaction.

Illustrative of the suitable soluble acid salts of the dopa species are the hydrochloride and sulfate. The hydrochloride salts are preferred. Among the suitable basic salts that can be used are the soluble alkali metal salts and the alkaline earth metal salts. The sodium and potassium salts are preferred. Any inorganic or organic acid or base can be used to adjust the pH of the dopa species premix solution, provided that the agent used does not interfere in the reactions. Suitable bases are ammonium and sodium hydroxide and mono-, di- and trialkanolamines, especially ethanolamines. Such acids are hydrochloric, phosphoric, tartaric, citric and lactic acids and their salts. Sodium hydroxide and hydrochloric acid are preferred.

The dopa species (or dopa species salt) concentration in the initial reaction medium is from about 2 mg/ml up to about the solubility limit of the dopa species in the reaction medium. Preferably, its concentration is from about 5 to about 25 mg/ml in the initial reaction medium, most preferably from about 5 to about 15 mg/ml.

The dopa species is selected from dopa and substituted homolog or analog dopa compounds. Typical dopa species suitable for use herein include alpha alkyl dopa having 1 to 4, preferably 1 to 2, carbon atoms in the alkyl groups, epinephrine (adrenaline) and dopa alkyl esters having 1 to 6, preferably 1 to 2, carbon atoms in the alkyl group.

Alpha alkyl dopa is oxidized by the ferricyanide oxidant in analogous manner to dopa, to form 5,6-dihydroxy-2-alkylindole, which forms melanin by aerobic oxidation.

Epinephrine, which has the structure:

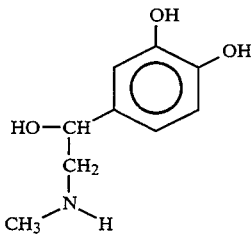

reacts with the ferricyanide oxidant to form adrenochrome. It is believed that adrenochrome rearranges to form adrenolutin and various indolic and/or isatinic derivatives.

In the case of the dopa alkyl esters, oxidation by ferricyanide proceeds to form the corresponding esters of 5,-dihydroxindole-2-carboxylic acid, which reaction proceeds without decarboxylation, i.e., there is no release of carbon dioxide. This ester of 5,6-dihydroxyindole-2-carboxylic acid then polymerizes to melanin by aerobic oxidation.

The Oxidant Component

Suitable ferricyanide oxidants include soluble ammonium, alkali metal and alkaline earth metal salts, especially ammonium, sodium and potassium salt of ferricyanide. Advantageously, the reduced form of ferricyanide—ferrocyanide—present in the aqueous solution following the reaction will not further react with the melanin precursor in the aqueous system, thereby maximizing the formation of the melanin precursor and hence increasing the overall efficiency of the process.

The oxidant is quite reactive towards the dopa species present in the reaction medium during the process. Thus, the initial reaction between the dopa species and the oxidant goes essentially to completion within less than five minutes, most likely in less than one minute, and might even be regarded as instantaneous in some instances. For this reason, intermediates in the postulated reaction schemes leading to the formation of the melanin precursor are short-lived in the reaction media and not available for inter-reaction. Accordingly, in the process of the present invention, unwanted side reactions are prevented or greatly limited.

The oxidant reactant is present in the initial reaction medium at a substantially stoichiometric equivalent concentration, as further described below.

A greater than about a stoichiometric equivalent amount of oxidant relative to the dopa species employed is not recommended, as the excess oxidant will react with the melanin precursor. The dopa species (dopa or substituted dopa) in an excess stoichiometric equivalent amount relative to oxidant is preferred to ensure that unreacted oxidant does not remain following the reaction. An excess of the dopa species does not appear to affect the process performance, although unreacted substituted dopa would tend to reduce the overall efficiency of the process and increase the desirability of a post-oxidative treatment. Generally, the stoichiometric equivalent ratio on a molar basis of the dopa species to ferricyanide initially present in the reaction medium will be from about 1.25:1 to 0.95:1, preferably from about 1.1:1 to 1:1, most preferably from about 1.05:1 to 1.01:1.

When the oxidative hair dye modifiers are optionally incorporated in the ferricyanide reaction mixture, it is believed that the direct dye, primary intermediate and/or coupler hair dye compounds react with one or more of the intermediate reaction products prior to rearrangement of the cyclized intermediate. Further, it is believed that a portion of the dopa species initially present in the reaction medium is reacted to completion to form 5,6-dihydroxyindole or the equivalent analog melanin precursor. Theoretically, when the optional oxidative hair dye components are incorporated, the initial reaction medium should contain between two to four molar equivalents, i.e., between 0.5 to 1 stoichiometric equivalents of oxidant relative to the dopa species based on complete conversion of dopa to the melanin precursor. Accordingly, the stoichiometric equivalent ratio on a molar basis of the dopa species to oxidant initially present in the reaction medium is generally from about 1:1 to 2:1, preferably from about 1.2:1 to 1.8:1, most preferably from about 1.3:1 to about 1.7:1.

The Buffering Agent Component

Inasmuch as the pH of the reaction medium will fall during the reactions, it is necessary to provide a sufficient amount of a buffering agent in the reaction medium to maintain the requisite pH. In the ferricyanide oxidation process, it is critical to maintain the pH of the aqueous reaction medium between about 6 to about 8.5, and especially alkaline to about 8.5.

In addition to controlling reaction medium pH within the aforesaid limits, the buffers employed are believed to assist in the formation of the melanin precursors. Thus, it has been observed that as the concentration of the buffers in the reaction medium increases, the rate of the rearrangement of dopachrome and its analog also increases. Thus, the buffers potentiate the rearrangement reaction, thereby decreasing the time for the generation of the melanin precursor, which permits the hair dyeing process to be completed within about one hour from the onset of the dopa species oxidant reaction. Typically, the buffer is present in an amount in excess of that needed to buffer the reaction mixture. Preferably, then, it is desirable to provide 2 to 25 times, especially 5 to 20 times, as much of these particular buffers as would be needed merely to maintain the reaction mixture pH within the prescribed limits.

Buffers found to be suitable include ammonium and alkali metal phosphates, bicarbonates, carbonates and, to a lesser extent, borates. Also suitable are aminic buffers such as N-2-hydroxyethyl]piperazine-N'-2-ethanesulfonic acid](DEPES),N-2-acetamido -2-aminoethane sulfonic acid (ACES), tris hydroxymethyl aminomethane (TRIZMA) and N-trist hydroxymethyl]-methyl-3-aminopropane sulfonic acid (TAPS). The ammonium and alkali metal carbonates and bicarbonates are suitable, even though not typically employed in the stated pH range. The preferred buffers are sodium and potassium carbonate, bicarbonate or phosphate when the oxidant is ferricyanide and phosphate buffer with the permanganate oxidant. Other buffers suitable for maintaining reaction medium pH and to potentiate the rearrangement reaction may exist which may be determined by simple experimentation, as herein disclosed in the examples.

The Process Parameters

It should be understood that the ability to obtain the necessary melanin precursor concentration depends on both its yield and the amount of the dopa species available for conversion. Thus, a lower melanin precursor yield would be acceptable when a high initial dopa species concentration is provided in the reaction medium. Conversely, a relatively high melanin precursor yield would be needed if a low dopa species concentration is used.

For permanently dyeing hair, the melanin precursor is converted to melanin in situ while the hair dyeing composition is in contact with the hair. Thus, the process should be viewed as a dynamic one in which the various reactions leading to melanin proceed simultaneously. Accordingly, the concentration and molar yield of the melanin precursor based on the dopa species formed in the hair dye composition is not directly measurable unless the subsequent melanin-forming reaction is prevented. Even then, the measurement of the yield is complex in view of the number of competing reactions and the number of chemical species present. The measurement are especially complex and difficult for the substituted dopa species, in particular, epinephrine, and when the reaction mixture further includes a direct dye, coupler or primary intermediate. Similarly, amount and yield of melanin not easily quantitatively measurable because it is formed in the hair. On the other hand, the effectiveness of the process may be determined by measuring the change in hair color when a hair swatch is treated in accordance with the process. Further, such evaluation is an indication of the amount of melanin that has formed in the hair shaft, and hence the amount of precursor that has diffused into the hair shaft during the treatment. The test procedure is discussed further below. As a guide to the successful practice of the invention, applicants have found that a perceptible color change to hair occurs within one hour of application to the hair. A suitable melanin precursor molar yield is typically obtained when the initial dopa species concentration is from about 2 mg/ml up to its solubility limit in the reaction medium.

In the case where dopa alone is contained in the reaction medium (i.e., other direct dyes, couplers and/or primary intermediates are not present), it has been found that a perceptible color change to hair occurs within one hour of application to the hair when a peak 5,6-dihydroxyindole (DHI) concentration obtained in the hair dyeing composition is at least about 1.5 mg/ml. This peak DHI concentration, which may be regarded as a practical minimum, occurs typically during the early stage of the reactions described above, normally within the first 30 minutes, preferably within the first 20 minutes of reactant admixture. An initial dopa concentration of about 3 mg/ml, coupled with DHI molar yield of about 65%, is suitable to achieve the practical minimum peak DHI level in the aqueous composition. It should be understood that the peak DHI concentration is measured during the reactions occurring in the reaction medium and in isolation from the hair. As measured by HPLC, molar yields of DHI are typically from about 50 to 70%, with molar yields of the by-product dihydroxyindole carboxylic acid being from about 7 to 9%, both yields being based on conversion of dopa. Preferably, the peak DHI concentration obtained in the aqueous composition is above about 2.5 mg/ml, most preferably above about 4 mg/ml. DHI molar yields above about 50% and initial dopa concentrations from about 5 mg/ml to the solubility limit in the reaction medium of the dopa species employed are preferred to establish levels of DHI in the hair dye composition suitable to generate a hair dyeing amount of melanin. Of course, the incorporation of the direct dye, primary intermediate and/or coupler hair dye components in the reaction medium will decrease the amount of the 5,6-dihydroxyindole melanin precursor obtained, in favor of other melanin precursors that are not easily quantifiably measured.

For the substituted dopa compounds, a suitable melanin precursor molar yield is typically obtained when the initial substituted dopa concentration is from about 2 mg/ml up to its solubility limit in the reaction medium. Thus, from in vitro experiments it has been found that an initial concentration of alpha methyl dopa of 2 mg/ml yields about 1.5 mg/ml methylindole, which corresponded to about a 90% molar yield. When the initial alpha-methyl dopa concentration was about 8–9 mg/ml, the molar yield was about 60–65%. Similarly, an initial dopamethylester concentration of 2 mg/ml was found to provide dihydroxyindole-2-carboxylic acid methyl ester at about 95% molar yield.

Melanin Promoting Agents

The formation of melanin from the melanin precursor may be promoted by application of a melanin promoting agent or agents, as described below.

Thus, certain transition metal and zinc ions, for example, copper, zinc, nickel, cobalt and iron ions, accelerate the conversion of the melanin precursor to melanin. As used herein "transition metal" is deemed to include zinc. Solutions of the salts of these ions applied to hair in conjunction with the applications the dye composition of this invention to hair result in a deepening of the color obtained. The transition metal salt ions effect a color change to the hair more rapidly than when they are not used. Typically, the color change is obtained in less than about 30 minutes, preferably less than about 15 minutes. Because the precursor that is formed is used more efficiently, lower melanin precursor concentrations are suitable in obtaining significant color in a single treatment. $Cu^{++}$ salts and, to a lesser extent, $Fe^{++}$ salts are preferred.

The metal salt solution may be applied to the hair for a predetermined period of time, typically for about 1 to about 10 minutes, before or after treatment with the hair dyeing composition. As a general rule, application of the metal ion solution during the contact of the hair with the hair dye composition is not preferred, as the metal ion causes melanin to form outside the hair shaft. However, in some instances such simultaneous application might be useful, especially with a metal ion agent such as zinc which more slowly effects melanin promotion.

Excess metal salt is removed from the surface of the hair by rinsing or shampooing prior to the application of the hair dye composition. It is suitable to incorporate the metal ions into a shampoo formulation for pre- or post-treatment, in which event a water rinse will suffice to remove the excess. The metal ions are believed to penetrate into the hair shaft and thus be available to rapidly accelerate the conversion of diffused precursor to melanin upon subsequent treatment with the hair dye composition described herein. The metal salt solution typically contains from about 0.01 to about 1% of the metal salt.

Colors

The use of dopa alone as the starting reagent to obtain the melanin precursor 5,6-dihydroxyindole is suitable to produce a melanin that dyes hair black or gray. It is unable to produce chromatic colors. When the substituted dopa compounds are employed, the ferriyanide hair dyeing process advantageously dyes hair a range of shades depending upon the selection of the starting substituted dopa species. Thus, colors ranging from light to medium brown to black with red, blue, green and yellow tones are possible, depending on the choice of the starting material and the contact time of the hair dye composition on the hair. Alpha methyl dopa has been found to provide a dark brown color, while medium brown has been obtained with dopa methyl ester, and light brown with epinephrine.

The addition of one or more conventional direct dyes, hair dye couplers or hair dye primary intermediates to the initial reaction mixture provides a further means for introducing chromatic colors to the melanin obtained in the ferricyanide process. Thus, colors ranging from light to medium brown to black with red, blue, green and yellow tones are possible, depending on the choice of the starting materials and the contact time of the hair dye composition on the hair.

The various dopa species suitable for use herein may be mused singly or in admixture, alone or in combination with one or more of the oxidative hair dye modifiers in order to achieve a desired color.

Hair Dye Modifiers

One or more direct dyes, hair dye primary intermediates and/or hair dye couplers with the reaction medium may be employed in the ferricyanide process, with a view towards modifying the ultimate color effect produced on the hair. Thus, it is believed that these conventional hair dye components react with the various species formed during the reaction, thereby incorporating one or more additional chromophoric substituent groups within the ultimate melanin species. The presence of the chromophoric groups provides tonality modification so that a broad array of colors is available to the user. Because the reaction with the direct dyes, primary intermediates and/or couplers may prevent cyclization, nitrogenous phenolic melanin precursors are likely obtained in lieu of indolic melanin precursors.

The concentration of the direct dyes, couplers and/or primary intermediates or couplers is less than about 10 mg/ml, and preferably is present in the reaction medium from about 0.01 to about 5 mg/ml, most preferably from about 0.05 to about 2 mg/ml. The amount of these hair dye components should not be so great as to prevent the formation of indolic melanins.

The table below lists some of the preferred primary intermediates and couplers for use in the ferricyanide process.

TABLE 1

| Preferred Primary Intermediates and Couplers | |
|---|---|
| Primary Intermediates: | p-phenylenediamine |
| | P-aminophenol |
| | o-aminophenol |
| | N,N-bis(2-hydroxyethyl)-p-phenylenediamine |
| | 2,5-diaminopyridine |
| | p-toluenediamine |
| Couplers: | resorcinol |

TABLE 1-continued

| Preferred Primary Intermediates and Couplers |
|---|
| m-aminophenol |
| α-naphthol |
| 5-amino-o-cresol |
| 2-methylresorcinol |
| N-acetyl dopa |
| 4,6-di(hydroxyethoxy)-m-phenylenediamine |
| m-phenylenediamine |

Suitable direct dyes include, for example, nitro dyes, azo dyes, and anthraquinone dyes.

Optional Adjuvant Constituents

The compositions employed in the ferriyanide oxidation process may also include in the hair dye composition one or more optional ingredients, which may be provided in one or more additional containers of the kit for admixture by the user into the aqueous reaction mixture, or, if compatible, may be incorporated into the oxidant or dopa premix solutions.

Well-known conventional additives usually employed in oxidative hair coloring compositions such as organic solvents, thickeners, surface-active agents, pH adjusting agents, antioxidants, fragrances and chelating agents may be included in the compositions of the invention.

The ferricyanide compositions may also include an organic solvent as a cosolvent. The organic solvent may assist in the dissolution of the components of the composition, and is present typically in an amount up to about 30%, preferably up to about 15%. A desirable range is from about 0.1 to about 15%, most preferably from about 1 to 10%.

Suitable solvents are mono- and polyhydric alcohols, for example, ethyl alcohol, isopropyl alcohol, propylene glycol, benzyl alcohol, etc., and glycol ethers, such as 2-butoxyethanol, ethylene glycol monoethyl ether and diethyleneglycol monoethyl ether.

Surface-active agents employed in the dyeing compositions of this invention can be anionic, nonionc, cationic, amphoteric or zwitterionic. By way of examples of the various types of surface-active agents, there can be mentioned: higher alkylbenzene sulfonates; alkylnaphthalenesulfonates; sulfonated esters of alcohols and polybasic acids; taurates; fatty alcohol sulfates; sulfates of branched chain or secondary alcohols; alkyldimethylbenzylammonium chlorides, salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester, myristyl sulfate; glyceryl monostearate; triethanolamine oleate, sodium salt of palmitic methyl taurine; cetyl pyridinium chloride; lauryl sulfonate; myristyl sulfonate, lauric diethanolamide; polyoxyethylene stearate; ethoxylated oleoyl diethanolamide; polyethylene glycol amides of hydrogenated tallow; stearyldimethyl benzyl ammonium chloride; dodecylbenzene sodium sulfonate; triethanolamine salt of p-dodecylbenzene sodium sulfonate; triethanolamine salt of p-dodecylbenzene sulfonate; nonylaphthalene sodium sulfonate; dioctyl sodium sulfonsuccinate; sodium N-methyl-N-oleoyl taurate; oleic acid ester of sodium isothionate; sodium dodecyl sulfate; the sodium salt of 3-diethyl tridecanol-6-sulfate and the like. The quantity of surface-active agent can vary over a wide range, such as from about 0.05% to 15% and preferably from about 0.10 to 5% by weight of the composition. The anionic and nonionic surfactants are employed typically as emulsifiers, while the cationic surfactants are useful to impart a hair conditioning benefit to the hair. Care must be exercised when anionic and cationic surfactants are both incorporated, in view of possible incompatibility.

Chelating and sequestering agents include, for example, ethylenediaminetetraacetic acid, sodium citrate, etc., and are present in amount of under about 1%.

A thickening agent may also be incorporated in the dyeing composition, which may be one or several of those commonly used in hair dyeing. These are exemplified by such products as sodium alginate or gum arabic, or cellulose derivatives, such as methylcellulose, e.g., Methocel 60 HG, or the sodium salt of carboxymethylcellulose, or hydroxyethyl-cellulose, e.g., Cellosize QP-40 or acrylic polymers, such as polyacrylic acid sodium salt, or inorganic thickeners, such as bentonite. The quantity of this thickening agent can also vary over a wide range, even as high as 20%. Ordinarily it will range from about 0.1 to 5% by weight of the composition. The viscosity of the composition may vary from about 1 cp to about 100,000 cps. For a typical lotion formulation, composition viscosity is between about 100 cps to about 10,000 cps, at which viscosity the composition can be applied to the hair without running or dripping.

In alkaline solution the dopa salt may be somewhat susceptible to oxidation, for example, by air. Accordingly, a small amount of an antioxidant may be included in the alkaline dopa premix. In such instances the amount of oxidant in the oxidant premix might be increased to neutralize the remaining antioxidant upon admixture of the dopa species and the oxidant premixes.

This list of optional ingredients is not intended as limiting. Other suitable adjuvants for inclusion in the hair dye composition are recited, for example, in Zviak, *The Science of Hair Care* (1986) and Balsam and Sagarin, *Cosmetics: Science and Technology*, Vol. 2 (Second Edition 1972).

THE POST-OXIDATIVE TREATMENT

It has been discovered that the amount of melanin pigment formed from the dopa species/ferricyanide oxidation process can be increased to obtain a higher degree of permanent coloring by applying an effective amount of an oxidizing solution to the hair which has already been permanently colored by the ferricyanide oxidation process described in detail above.

A wide variety of oxidizing agents can be employed including, for example, nitrites, persulfates, periodates, iodates, ferricyanide and perborates. Generally, these oxidants will be employed as salts, typically ammonium, alkali metal or alkaline earth metal salts. Alkali metal salts are generally preferred and, of these, sodium salts are most preferred because they are readily available and easily soluble in water. Sodium periodate is the most preferred oxidizing agent because it is fast acting and provides high yields of melanin pigment.

oxidizing metal salts can also be employed for post-oxidative treatment. Water soluble salts, such as cupric chloride, sulfate or acetate have been found to be especially effective.

Hydrogen peroxide can be used as an effective post-oxidant in association with a soluble iodide salt such as sodium iodide, The iodide salt is incorporated into the dopa species-ferricyanide composition and, apparently a sufficient amount of the salt remains on the hair even after rinsing to catalyze the peroxide oxidation.

The concentration of the oxidant in the post-oxidative compositions of the invention and the pH of the compositions will depend principally on the oxidant selected. Generally an oxidant concentration of from about 0.1% to about 10%, preferably 1% to 5% aqueous solution will be suitable. With hydrogen peroxide, the oxidant concentration is normally from about 0.1% to 6%, preferably 0.1% to 3%. It will be employed in association with 0.01 to 1% concentration of the iodide salt in the dopa species-ferricyanide composition.

The pH may range from about 2 to about 11. With a periodate oxidant the preferred pH is from 5 to 8.

With cuprous salts the concentration is from about 0.01% to above 5% at a pH of from about 2 to about 11.

The post-oxidative treatment is conducted after rinsing but before drying the treated hair. Preferably, although not necessarily, the treatment is conducted concurrently with shampooing. Accordingly, the post oxidative compositions may contain a surfactant such as those mentioned above. If the surfactant is oxidation resistant, it may be employed in the same solution as the oxidizing agent. If a surfactant which is not oxidation resistant is selected, it will be in a separate container.

As with the ferricyanide oxidation, the post-oxidative treatment is conducted by applying the post-oxidative composition to the hair and maintaining contact until the desired color is attained. Normally the period of contact is from about 1 to 10 minutes, preferably 2 to 5 minutes.

The post-oxidative composition may contain in addition to a surfactant, if employed, any of the adjuvants mentioned above in connection with the description of the ferricyanide process.

THE HAIR DYEING KIT PRODUCT

A hair dyeing kit in accordance with this invention will contain in a package a plurality of containers comprising the reactants for the initial ferricyanide treatment and the subsequent post-oxidative treatment.

For example, the kit may include a first container containing the selected dopa species or mixture thereof and a second container containing the oxidant. The buffer for the ferricyanide oxidation may be separately packaged in a third container or may be present in either the first or second container. The selected oxidant will be in still another container which may, as indicated above also contain a sufficient amount of a surfactant to be effective as a shampoo.

One or more additional containers may be provided in the kit to provide one or more of the optional adjuvants mentioned above. These optional constituents may also be in one of the other containers, barring any incompatibility.

While the kit may contain packets containing amounts, preferably premeasured, of dry powders for preparation of the various compositions, it is more convenient to provide the compositions in liquid form as solutions. Moreover, solutions containing premeasured quantities of the constituents facilitates their correct use by the consumer.

The consumer admixes the components of the kit, suitably as the aqueous solutions or as dry powders and water, according to written instructions, to obtain the aqueous reaction mixtures. The admixture may be conducted in a separate vessel supplied with or external to the kit, or may take place in a container of the kit adapted to provide sufficient head space for mixing. The reactants may also be admixed on the hair of the user.

In the examples, the colors are evaluated utilizing the standard Hunter Tristimulus values. In the Hunter method, the parameters a and b may be positive or negative and define the chromatic condition of the hair. Thus, the more positive the a value, the greater the redness of the hair, while a negative a value indicates greenness. Similarly, positive b values indicate yellowness, while negative b values indicate blueness. The L parameter is a measure of color intensity, and has a value of 0 for absolute black to 100 for absolute white. Generally, hair having an L value of about 15 or less is considered black, while an L value of about 60 is white. It should be understood that the L value scale is not linear, but rather is sigmoidal. Proximate to 0 and proximate to 100 hair color intensity apparent to the human eye varies minimally with unit changes in the L value. Between values of about 20 to about 50, hair color intensity varies significantly with unit changes in L value. Thus, the Hunter values are more sensitive in the region where the human eye is able to perceive color changes.

EXAMPLE 1

Gray hair (L=34.0; a=0.2; b=6.9) was dyed with hair dye compositions containing 0.69% potassium iodide together with 0.075g. of the dopa species shown in Table II below, 7.5 ml 0.1M HCl, and a second solution containing 0.9g potassium ferricyanide, 7.5 ml water and sufficient phosphate buffer to provide an initial pH of the hair due composition of 7.2, i.e., after mixing of the first and second solutions. The hair tresses were dyed by applying each of the compositions to a tress for:30 minutes. The tresses were then rinsed, post treated with a solution containing 3% hydrogen peroxide adjusted to pH 9.5 with sodium carbonate, again rinsed, shampooed with a conventional shampoo and dried. Hunter values of the dyed tresses are reported in Table II.

TABLE II

| No. | Dopa Species | Hunter Tristimulus Value | | | Color |
|-----|---|---|---|---|---|
| | | L | a | b | |
| A | α-Methyl dopa | 28.1 | 0.5 | 4.0 | Gray Brown |
| B | Epinephrine | 28.2 | −0.1 | 7.5 | Light ash brown |
| C | Dopa methyl ester | 31.4 | 0.4 | 5.4 | Gray |

EXAMPLE 2

A hair dye composition was provided by mixing a first solution containing 0.2 g dopa, 0.13 g $Na_2CO_3$, 0.5 g triethanolamine (TEA) and 0.18 g 2-nitro-p-phenylene diamine in 10 g total solution with a second solution containing 1.2 g potassium ferricyanide, 0.06 g $Na_2CO_3$ and 0.02 g citric acid in 10 g total solution. The pH after mixing was approx. 7–8. The composition was applied to (gray) hair, left for 20 minutes and rinsed off. The swatch was contacted with an aqueous solution of $NaIO_4$ (5%) for 2 minutes, rinsed and dried. A reddish brown color was imparted to the hair.

| Hunter Tristimulus Values | L | a | b | |
|---|---|---|---|---|
| before dyeing | 39.0 | 0.25 | 6.75 | gray |
| after dyeing | 19.45 | 4.24 | 3.93 | reddish brown |

EXAMPLES 3–5

Hair dye compositions were prepared as described in Example 2, but 2-nitro-p-phenylene diamine in the first solution was replaced by a coupler (m-amino phenol) or a primary intermediate (p-amino phenol, modifier 1) and a direct dye (modifier 2), of the structure and concentrations listed in Table IV. Hair was dyed as described in Table III. The results are set forth in Table III. The color of the swatches remained essentially unchanged after several cycles of shampooing.

TABLE III

Dyeing of bleached (bl) and gray (gr) hair with DOPA (1%), two modifiers and ferricyanide[a]

| No. | Modifier 1 [%] | Modifier 2 [%] | hair | Post-oxidative Hunter Tris. Val. | | |
|---|---|---|---|---|---|---|
| | | | | L | a | b |
| 3 | m-AP [0.2] | 2-Amino-5-nitro phenol [0.39] | bl | 19.0 | 5.2 | 9.0 |
| | | | gr | 22.1 | 2.5 | 10.5 |
| 4 | m-AP [0.2] | 4-Amino-3-nitro phenol [0.39] | bl | 18.6 | 5.7 | 7.4 |
| | | | gr | 18.8 | 4.3 | 7.2 |
| 5 | m-AP [0.2] | 5-Amino-2-math oxypyridine [0.31] | bl | 29.6 | 6.4 | 13.6 |
| | | | gr | 27.1 | 2.6 | 914 |

[a] Initial dyeing time 15 minutes; oxidative post-treatment 1% $NaIO_4$, 2 minutes

EXAMPLE 6

10 mg 4-S-cysteaminylcatechol hydrochloride (0,045 mmole), 9 mg dopa (0.045 mmole), 59 mg potassium ferricyanide and 35 mg sodium bicarbonate were dissolved in 5 ml water. The pH was about 7.8. The solution was applied to white hair and left for 20 minutes. The hair was rinsed and dried with heat (hairdryer). The hair was dyed to a reddish brown color.

Hunter Tr. Val. L 27.5 a 8.6 b 6.3 reddish brown

The procedure was repeated with a similar swatch of white hair with the exception that after rinsing and before drying the hair was exposed to an aqueous solution of 1% sodium periodate for 2 minutes. After drying with heat (hairdryer), the hair had a warm brown color.

Hunter Tr. Val. L 23.3 a 5.6 warm brown

What is claimed is:

1. A method of increasing the amount of melanin formation in hair which has been permanently dyed with melanin comprising the steps of
   (a) forming a melanin precursor by reacting a dopa species selected from the group consisting of dopa, epinephrine, alpha alkyl dopa having 1 to 4 carbon atoms in the alkyl group and dopa alkyl esters having 1 to 6 carbon atoms in the alkyl group with a soluble ammonium, alkali metal or alkaline earth metal ferricyanide salt in an aqueous medium containing a buffering agent, the concentrations of the dopa species and the ferricyanide salt being in amounts effective to provide a hair coloring concentration of a melanin precursor in the aqueous reaction medium, said dopa species and ferricyanide salt being present in a stoichiometric equivalent ratio of from about 1:1 to 2:1 dopa to ferricyanide salt, said buffering agent being in an amount to maintain the pH of the aqueous reaction medium between about 6 to about 11;
   (b) contacting the hair with the aqueous reaction medium and allowing the melanin precursor to diffuse into the hair in an amount sufficient to generate a hair coloring amount of melanin;
   (c) permanently coloring the hair by allowing melanin precursor present in the hair to form melanin, and
   (d) contacting the hair with an aqueous solution of a post-oxidant at a pH of from about 2 to about 11 for a period or from about 1 to about 10 minutes, the concentration of the post-oxidant being from about 0.1% to about 10% thereby to oxidize previously unoxidized melanin precursor to melanin, said post-oxidatively treated hair having a more intense coloration than hair not so treated.

2. A method as in claim 1 wherein the post-oxidant is sodium periodate.

3. A method as in claim 1 wherein the post oxidant is a water soluble cupric salt.

4. A method as in claim 1 wherein the aqueous reaction medium formed in step (a) additionally contains from about 0.01% to about 1% of a water soluble iodide salt and the post oxidant is a 0.1 to 6% hydrogen peroxide solution.

5. A method as in claim 1, 2, 3 or 4 wherein the dopa species is 3,4-dihydroxyphenylalanine.

6. A method as in claim 5 wherein the post-oxidant composition contains a sufficient amount of surfactant to be effective as a shampoo.

7. A hair dyeing kit for permanently dyeing hair with melanin from a melanin precursor which includes in a single package a plurality of containers, the kit comprising (a) a first container containing an aqueous solution of a dopa species selected from the group consisting of dopa, epinephrine, alpha alkyl dopa having 1 to 4 carbon atoms in the alkyl group and dopa alkyl esters having 1 to 6 carbons in the alkyl group, (b) a second container containing a water-soluble ammonium, alkali metal or alkaline earth metal ferricyanide-oxidant, (c) in one of said containers or in an additional container a pH control agent in an amount to provide a pH of from about 6 to about 11 when the contents of the containers are mixed, the concentration of the dopa species present in the kit being in an amount effective to form sufficient melanin by oxidation of melanin precursor to permanently dye the hair, said dopa and ferricyanide oxidant components in the kit being present in a stoichiometric equivalent ratio of from about 1:1 to about 2:1 dopa to oxidant, and (d) a third container containing an aqueous solution of a post-oxidant having a concentration of from about 0.1% to about 10% and having a pH of from about 2 to 11.

8. A kit as in claim 7 wherein the post-oxidant is sodium periodate.

9. A kit as in claim 7 wherein the post oxidant is a water soluble cupric salt.

10. A kit as in claim 7 wherein the solution formed by mixing the contents of the first and the second container contains from about 0.1% to about 1% of a soluble iodide salt and the post oxidant is a 0.1 to 6% hydrogen peroxide solution.

11. A kit as in claim 7, 8, 9 or 10 wherein the dopa species is 3,4-dihydroxyphenylalanine.

12. A kit as in claim 11 wherein the aqueous solution of post-oxidant contains a sufficient amount of surfactant to be effective as a shampoo.

* * * * *